(12) United States Patent
Guieze et al.

(10) Patent No.: US 8,109,158 B2
(45) Date of Patent: Feb. 7, 2012

(54) SAMPLING APPARATUS

(75) Inventors: Paul Guieze, Fontenailles (FR); David MacWilliam, Aberdeenshire (GB); Kostas Kotzakoulakis, Chania (GR)

(73) Assignee: Schlumberger Technology Corporation, Sugar Land, TX (US)

( * ) Notice: Subject to any disclaimer, the term of this patent is extended or adjusted under 35 U.S.C. 154(b) by 669 days.

(21) Appl. No.: 11/576,478

(22) PCT Filed: Sep. 28, 2005
(Under 37 CFR 1.47)

(86) PCT No.: PCT/EP2005/010580
§ 371 (c)(1),
(2), (4) Date: Apr. 21, 2009

(87) PCT Pub. No.: WO2006/037565
PCT Pub. Date: Apr. 13, 2006

(65) Prior Publication Data
US 2011/0061475 A1 Mar. 17, 2011

(30) Foreign Application Priority Data
Oct. 7, 2004 (EP) .................................... 04292389

(51) Int. Cl.
*G01N 1/22* (2006.01)
(52) U.S. Cl. ........................................................ 73/864
(58) Field of Classification Search .............. 73/863.33, 73/152.23, 863.32
See application file for complete search history.

(56) References Cited

U.S. PATENT DOCUMENTS

| | | | | | |
|---|---|---|---|---|---|
| 2,406,192 | A | * | 8/1946 | Cantrell, Jr. ................ | 73/863.02 |
| 2,906,126 | A | * | 9/1959 | Brown ........................ | 73/863.02 |
| 4,210,015 | A | | 7/1980 | Euzen et al. | |
| 6,182,505 | B1 | * | 2/2001 | Segeral ........................ | 73/61.44 |
| 6,212,948 | B1 | * | 4/2001 | Ekdahl et al. .............. | 73/152.18 |
| 2004/0112150 | A1 | | 6/2004 | Germond | |
| 2005/0087027 | A1 | * | 4/2005 | Widmer .................... | 73/863.02 |

FOREIGN PATENT DOCUMENTS
FR 2792071 4/1999

* cited by examiner

*Primary Examiner* — Hezron E Williams
*Assistant Examiner* — Mark A Shabman
(74) *Attorney, Agent, or Firm* — Mathias Abrell; Darla Fonseca; Jeff Griffin

(57) ABSTRACT

A sampling apparatus for sampling a fluid enriched in a selected phase from a multiphase fluid mixture flowing into a main pipe, the multiphase fluid mixture containing at least the selected phase and one other phase, the apparatus comprising: —a sampling arrangement: for taking a fluid sample of the multiphase fluid mixture flowing into the main pipe, —a sample chamber having a variable volume for collecting the fluid sample of the multiphase fluid mixture and letting settle by gravity the fluid sample into the fluid enriched in the selected phase and at least another phase enriched fluid, and —a valve manifold coupling the sampling arrangement to the sample chamber for driving the fluid sample in the sample chamber and for driving the fluid enriched in the selected phase to a sample outlet and the other phase enriched fluid back to the main pipe.

18 Claims, 2 Drawing Sheets

SAMPLING APPARATUS

FIELD OF THE INVENTION

The invention relates to an apparatus for sampling a single phase from a multiphase fluid mixture.

A particular application of the invention relates to the sampling of the various phases of a multiphase fluid mixture from a hydrocarbon well. Such a multiphase fluid mixture typically comprises three phases: an aqueous phase, a liquid hydrocarbon phase and a gaseous hydrocarbon phase.

BACKGROUND OF THE INVENTION

After a hydrocarbon well has been drilled and made safe, various operations are generally carried out:
 well testing operations (serving to characterize the various components of the effluent flowing out of well, and to estimate the production capacities of the well), and subsequently
 well producing operation as long as the oil produced is satisfactory in term of quality, flowing rate, etc . . . .

During these operations, the composition of the effluent varies. The effluent that is initially collected is essentially made up of water. Subsequently, the percentage of aqueous residue decreases gradually, and the composition of the effluent becomes enriched with oil and with gas. Thus, the effluent is a multiphase fluid mixture. In addition, the multiphase fluid mixture may have complex flow regimes, e.g. mist, bubble, slug, churn flows, etc . . . in the well-bore or in the flowing lines.

During the testing and producing operation, an important concern is to identify and/or analyze as accurately as possible the various phases that constitute the multiphase fluid mixture. A preliminary step is to obtain a representative sample of the multiphase fluid mixture flowing out of the hydrocarbon well. Prior art systems disclosed in patents U.S. Pat. Nos. 6,182,505 and 6,212,948 relate to such sampling apparatus.

For sampling a phase from a multiphase fluid mixture, it is known to provide the pipe in which the multiphase fluid mixture flows with gravity traps (upper and lower traps) coupled to appropriate drain for collecting a particular phase. The representation of the phases collected by the gravity traps is questionable because the phases in the gravity traps are not refreshed continuously. In addition, the lower trap collects all heavy phases such as liquids (oil, water) and solids. These solids often plug the drain preventing further sampling, and if the heaviest liquid flow (water) is important, it is very difficult to drain the lighter one (oil) as the accumulation rate could be faster than the one draining.

It is also known to take a single shot sample (sampling cylinder) from the pipe in which the multiphase fluid mixture flows, to recondition the sample and to separate the phase later in a laboratory. The sample reconditioning in a laboratory consists in applying the pipe temperature and pressure for reaching the original thermodynamic equilibrium and therefore the original fluid phase compositions. The stabilized phases are then separated and transferred in several cells for physico-chemical measurements. This method does not enable to control the sampled volume of each phase, which could lead to an insufficient quantity of a given phase for the post-sampling measurements.

SUMMARY OF THE INVENTION

One goal of the invention is to propose a sampling apparatus that overcomes at least one of the shortcomings of the prior art.

According to the invention, the sampling apparatus is an active sampling apparatus collecting from a multiphase fluid mixture flowing into a main pipe a representative sample of a selected phase without changing its composition and state. The sampling apparatus takes a flowing fluids sample at a selected pipe position, collects the sample in a chamber of variable volume and enriches the sample in a given phase by dumping back to the main pipe the unwanted phases in an iterative process. The sampling apparatus comprises a phase detector for sensing the type of fluid taken and expulsed from the chamber and a volume measurement detector for measuring the volume of the chamber.

The sampling apparatus enables to take a significant and controllable volume of a selected phase for further analysis.

The sampling apparatus enables to maintain sample at line flowing conditions (pressure and temperature) during the entire sampling process in order to prevent compositional change due to mass transfers.

More precisely, the present invention relates to a sampling apparatus for sampling a fluid enriched in a selected phase from a multiphase fluid mixture flowing into a main pipe, the multiphase fluid mixture containing at least the selected phase and one other phase, the apparatus comprising:
 a sampling arrangement for taking a fluid sample of the multiphase fluid mixture flowing into the main pipe,
 a sample chamber having a variable volume for collecting the fluid sample of the multiphase fluid mixture and letting settle by gravity the fluid sample into the fluid enriched in the selected phase and at least another phase enriched fluid, and
 a valve manifold coupling the sampling arrangement to the sample chamber for driving the fluid sample in the sample chamber and for driving the fluid enriched in the selected phase to a sample outlet and the other phase enriched fluid back to the main pipe.

The sampling apparatus further comprises a temperature controlling arrangement for maintaining the sample chamber and the valve manifold at the multiphase fluid mixture temperature of the main pipe. The temperature controlling arrangement may comprise a thermal insulator, a heating device and a temperature regulator.

The sampling arrangement may comprise a sampling pipe adapted to be coupled to the main pipe, the sampling pipe comprising at least one sampling probe.

The sample chamber comprises a top port and a bottom port.

The valve manifold couples the sampling probe to the chamber and has a sample outlet for providing the fluid enriched in the selected phase. It comprises at least one probe valve coupling the sampling probe to a phase detector, a top port valve coupling the phase detector to the top port, a bottom port valve coupling the phase detector to the bottom port, and an outlet valve coupling the phase detector to the sample outlet.

The phase detector is for example an optical phase detector.

The sample chamber may comprise a piston that can be moved upward and backward within the sample chamber by a piston actuator. The variable volume is defined by the position of the piston within the sample chamber. The piston is separated from the sample chamber wall by an annulus for letting flow down a fluid present in the chamber towards the bottom port.

The sampling pipe may comprise a bottom, middle and top sampling probes respectively positioned in an inferior part, center part and superior part of the sampling pipe. The top, middle and bottom sampling probes face the flow of the multiphase fluid mixture.

The sampling pipe may further comprise a gas sampling probe positioned either in the middle part or in the superior part of the sampling pipe and in an opposite direction relatively to the bottom, middle and top sampling probes.

The sampling pipe may comprise one sampling probe having an adjustable position within the sampling pipe.

The sampling apparatus may further comprise a sensor for measuring the volume of the sample chamber (for example by measuring the position of the piston within the sample chamber).

The invention also relates to a sampling method for sampling a fluid enriched in a selected phase from a multiphase fluid mixture flowing into a main pipe, the main pipe being fitted with a sampling apparatus according to the invention. The sampling method comprises:
- a first step comprising the steps of taking a fluid sample of the multiphase fluid mixture by coupling one sampling probe to the sample chamber and increasing the volume of the chamber, and letting settle by gravity the fluid sample in the sample chamber into the fluid enriched in the selected phase and at least one unwanted phase enriched fluid,
- a second step comprising the steps of flushing at least one unwanted phase enriched fluid back to the main pipe by coupling the sample chamber to one sampling probe and decreasing the volume of the chamber,
- repeating the first and second step so as to obtain a given quantity of the fluid enriched in the selected phase in the sample chamber, and
- a third step comprising the step of expelling the fluid enriched in the selected phase out of the chamber by coupling the chamber to the outlet and decreasing the volume of the chamber.

Along the sampling operation, the sampling apparatus is maintained at the temperature of the multiphase fluid mixture flowing into a main pipe. In addition, the phases of the fluid flowing in and out of the sample chamber are monitored.

BRIEF DESCRIPTION OF THE DRAWINGS

The present invention is illustrated by way of example and not limited to the accompanying figures, in which like references indicate similar elements.

DETAILED DESCRIPTION OF THE INVENTION

Figure 1:
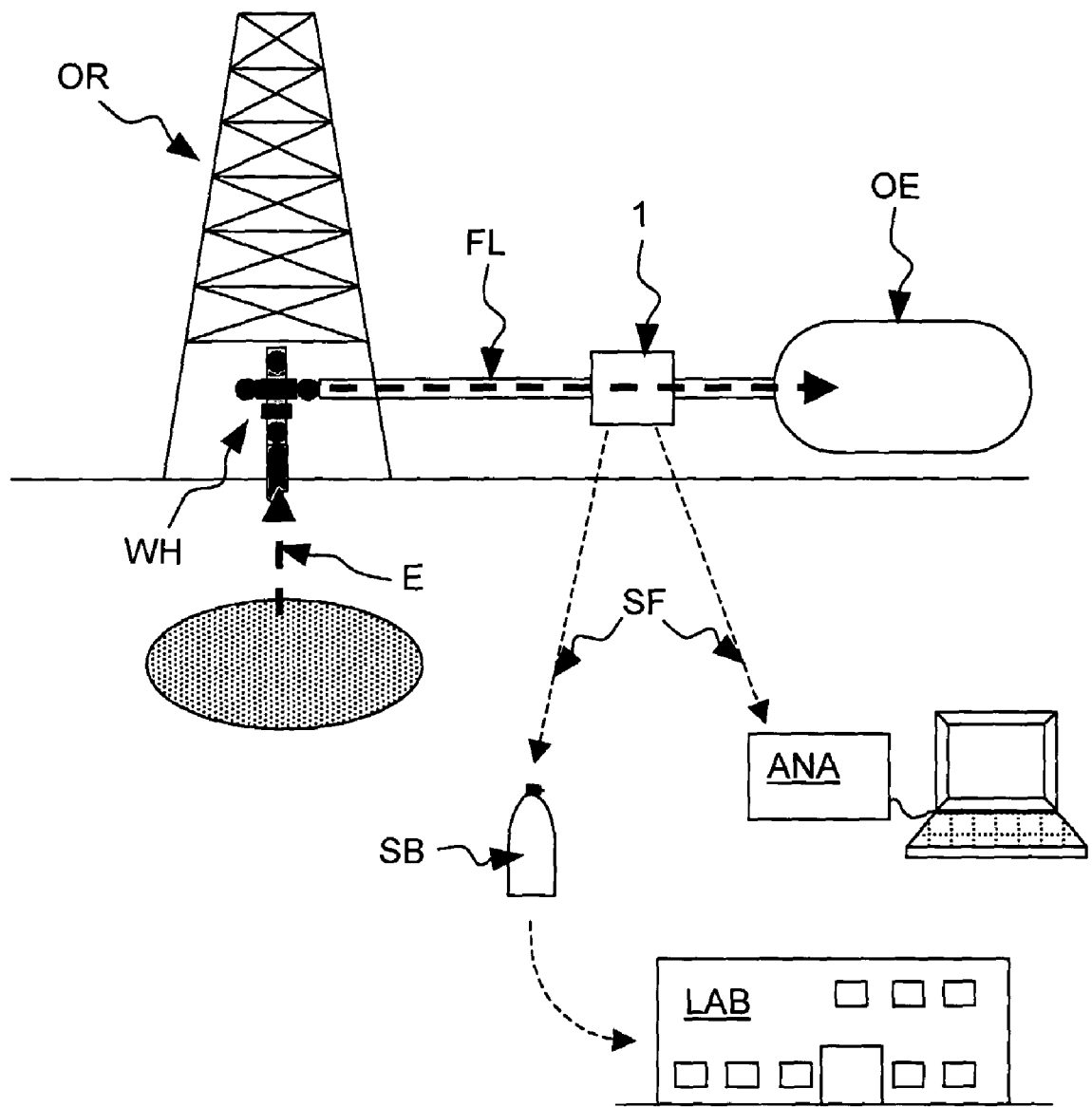
FIG. 1 is a schematic view of an hydrocarbon well and a well equipment comprising a sampling apparatus.

FIG. 1 shows schematically a hydrocarbon rig OR. An effluent E flows out of the well from a well head WH. The well head WH is connected to various well equipments OE through a main pipe FL. The well equipments may comprise any known well testing or well production equipments that will not be further described. The main pipe FL comprises a sampling apparatus 1 for sampling a fluid enriched in a selected phase from the effluent E constituted by a multiphase fluid mixture. The sampling apparatus provide a sampled fluid SF either to an appropriate analyzer ANA for on-field analysis, or into a sampling bottle SB for subsequent analysis by a laboratory LAB.

Figure 2:
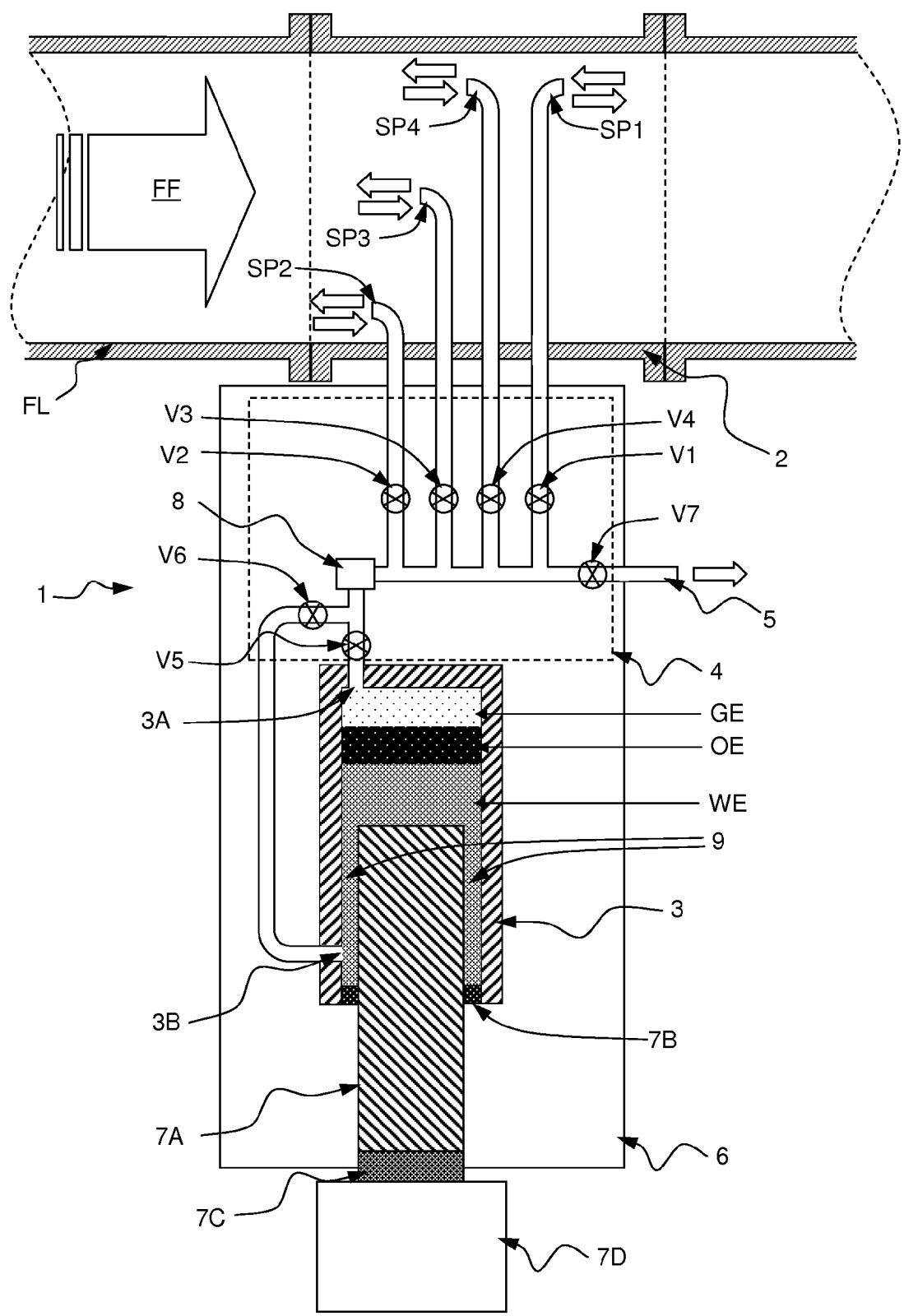
FIG. 2 schematically illustrates an apparatus for sampling a single phase from a multiphase fluid mixture according to the invention.

FIG. 2 schematically illustrates an apparatus for sampling a single phase from a multiphase fluid mixture according to the invention.

The sampling apparatus 1 comprises a sampling pipe 2, a sample chamber 3 of variable volume, a valve manifold 4 and a temperature controlling arrangement 6.

The sampling pipe 2 is adapted to be coupled to the main pipe FL, for example by known flanges/nipples and connections means. The sampling pipe 2 comprises four sampling probes: a gas sampling probe SP1, a bottom sampling probe SP2, a middle sampling probe SP3 and a top sampling probe SP4.

The bottom sampling probe SP2 is positioned in an inferior part of the sampling pipe 2. The middle sampling probe SP3 is positioned in a center part of the pipe. The top sampling probe SP4 is positioned in a superior part of the pipe. The top, middle and bottom sampling probes face the flow of the multiphase fluid mixture FF (i.e. the sampling tips of the top, middle and bottom sampling probes are directed upstream). The gas sampling probe SP1 is positioned in the middle part of the pipe and in the flow direction of the multiphase fluid mixture FF, namely in an opposite direction relatively to the top, middle and bottom sampling probes (i.e. the sampling tip of the gas sampling probe is directed downstream).

The sampling probes SP1, SP2, SP3 and SP4 allow sampling at different positions and directions in the main pipe. In particular, this positioning allows the capture of a predominant phase of the multiphase fluid mixture FF flowing into the main pipe 2, depending on its quality (gas, liquid) and on the flow regimes (mist, bubble, slug, churn flows, etc.). For capturing a predominant phase, one of the sampling probes can be selected by means of an integrated valve manifold as further described hereinafter.

The shape of the sampling pipe and the position of the sampling probes SP1, SP2 and SP3 on the same vertical line as shown in FIG. 2 are not limitative. Alternatively, the sampling pipe may have others shapes and configuration than the one shown on FIG. 2, for example it can be a pipe portion having a T-shape, elbows, etc . . . . In addition, the sampling probes position, as well as their numbers could vary depending on the fluid flow characteristics. In particular, the fluid flow characteristics depend on the position of the sampling point after an elbow or a straight of the main pipe, etc . . . . Such configuration of the main pipe can be expected and thus the position of the sampling probe can be adapted to the configuration.

Thus, the sampling probes SP1, SP2, SP3 and SP4 can be positioned according to various locations, angles and directions relatively to the fluid flow direction in the main pipe.

Advantageously, the sampling probes being steady positioned in the pipe and not involving any moving part, the sampling pipe and the sampling probes are very reliable regarding leaks and sticking problems whatever the multiphase fluid mixture flow characteristics (flow regime, pressure, temperature, composition . . . ).

The variable volume sample chamber 3 comprises a top port 3A and a bottom port 3B. The sample chamber 3 further comprises a piston 7A. The piston can move within the chamber so that the variable volume is defined by the position of the piston 7A within the sample chamber 3. The piston size and position within the chamber forms an annulus 9, enabling the fluid to enter or leave the chamber by the bottom port 3B. The chamber is sealed against the piston through a seal 7B.

Advantageously, the bottom port is placed at the piston seal level, which is the lowest point where the fluid present in the chamber (e.g. an heavy liquid phase) can be collected.

The piston 7A is actuated by a piston actuator 7D of the sampling apparatus. The piston actuator 7D may be a hydraulic driving arrangement comprising a hydraulic actuator to move the piston in the chamber and a loaded spring to move the piston out of the chamber. Alternatively, the sample chamber piston may be actuated by any other known mechanical drive (depending on the energy available).

The sampling apparatus further comprises a sensor (not shown) for measuring the volume (void volume) of the sample chamber. The sensor, for example an encoder, measures the position of the piston within the sample chamber. The value of this volume may be available for reading from a mechanical means (vernier) and/or a digital means (display).

The sample chamber with the piston is analogous to a high-pressure syringe, enabling the fluid sampled by one of the sampling probe to be sucked in the chamber and flushed out of the chamber. The chamber acts as a gravity separator for the sampled fluid.

For a particular application to the oilfield service industry, the hydrocarbon fluid mixture flowing in the main pipe is a mixture, which typically comprises three phases: an aqueous phase (water phase—in fact a water-enriched phase), a liquid hydrocarbon phase (oil phase—in fact an oil-enriched phase) and a gaseous hydrocarbon phase (gas phase). The sampled fluid (an hydrocarbon fluid mixture) penetrating in the chamber separates by gravity into a liquid layer and a gas layer GE. The liquid layer is constituted by a water-enriched layer WE (water with dissolved gases, salts and impurity, namely oil) and an oil-enriched layer OE (oil with dissolved gases and impurity, namely water). The liquid layer may further comprise an emulsion layer between the water-enriched layer and the oil-enriched layer. The thickness of the emulsion layer depends on the relative physical and chemical properties (e.g. density, interfacial tension, etc . . . ) of the oil and water phases.

The fluid sampled by one of the sampling probes can be sucked in the chamber either by the top port 3A or by the bottom port 3B. Preferably, the fluid is sucked by the top port 3A).

The fluid in the chamber can be flushed out of the chamber either by the top port 3A or by the bottom port 3B. Preferably, the lighter phases (gas phase but also oil-enriched phase) are flushed out of the chamber by the top port 3A, and the heavier phases (water-enriched phase but also oil-enriched phase) are flushed out by the bottom port 3B. Any sampling probe SP1, SP2, SP3, SP4 may be used for flushing the unwanted phase back into the main pipe FL.

Advantageously, the chamber may be designed for minimizing the dead volume.

The valve manifold 4 couples the sampling probes SP1, SP2, SP3 and SP4 to the sampling chamber 3. The valve manifold ensures both hydraulic and mechanical connections between the probes and the chamber.

The valve manifold 4 comprises a sample outlet 5 for providing a single phase enriched fluid, for example to an appropriate analyzer for a direct analysis of the fluid or to a shipping cylinder or bottle for a subsequent analysis in a laboratory.

The valve manifold 4 also comprises a phase detector 8 for determining the type of phase flowing from the sampling probes to the chamber and vice versa, or from the chamber to the outlet. Advantageously, the phase detector is an optical phase detector. The optical phase detector probe is fitted in the valve manifold so that all the fluids flowing in and out of the chamber are sensed.

The valve manifold 4 comprises at least one probe valve V1, V2, V3, V4, a top port valve V5, a bottom port valve V6 and an outlet valve V7.

The four probe valves V1, V2, V3, V4 respectively couple the gas SP1, bottom SP2, middle SP3 and top SP4 sampling probe to the phase detector 8.

The top port valve V5 couples the phase detector 8 to the top port 3A of the chamber 3.

The bottom port valve V6 couples the phase detector to the bottom port 3B of the chamber 3.

The outlet valve V7 couples the phase detector 8 to the sample outlet 5.

The valve manifold 4 allows the sampling probes selection, the sample chamber connection (top or bottom) and the sample outlet activation.

The valve manifold 4 allows the sampled fluid to be flushed out of the chamber to either the main pipe via one of the sampling probes SP1, SP2, SP3 or SP4, or to the sample outlet 5 for further use (direct analysis or shipping cylinder).

It is to be noted that the valve manifold 4 may be operated manually by an operator depending on the indication provided by the phase detector, or automatically or semi-automatically by a controlling arrangement (not shown). Said controlling arrangement may open and close the various valves and control the piston displacement according to the measurements made by the phase detector and the programmed phase to be predominantly sampled.

The sampling apparatus 1 further comprises a temperature controlling arrangement 6 for maintaining the sample chamber 3 and the valve manifold 4 at the temperature of the multiphase fluid mixture FF flowing into the main pipe FL. The temperature controlling arrangement 6 comprises a thermal insulator (not shown). The thermal insulator enables the valve manifold and the sample chamber to take advantage of the heat conducted by the sampled fluid via the various connections.

The temperature controlling arrangement may also comprise a heating device and a temperature regulator (not shown). This alternative may apply in case of too important temperature gradient between the main pipe and the sample chamber due to insufficient heat conduction.

In addition, both piston 7A and piston actuator 7D may be thermally insulated from the chamber by a piston thermal insulator 7C. Advantageously, the insulator is a special material joint.

The temperature controlling arrangement enables to keep the sample fluid at the same temperature that the multiphase mixture fluid flowing into the main pipe, thus avoiding mass transfers between the different phases governed by thermodynamic laws.

Advantageously, all wetted parts of the sampling apparatus are made with a proper alloy to provide the best chemical resistance and inertness, and the best mechanical resistance. The maximum operating pressure and temperature depend on the application, e.g. in oilfield industry application the sampling apparatus operates for pressure up to 700 bar and temperature up to 150° C.

The hereinbefore described sampling apparatus operates as follows.

After having connected the sampling apparatus to a main pipe of a hydrocarbon well, a sampling operation is performed according to a first step. At the beginning, all the valves are in a closed state. The sampling operation takes predominantly a fluid sample enriched in a selected phase out of the multiphase fluid mixture flowing into the main pipe. Depending of the phase selected to be sampled, a particular sampling probe is selected among the four sampling probes SP1, SP2, SP3 and SP4. The selection of a sampling probe is performed by the valve manifold 4.

For example, for taking a sample of:
a gas enriched fluid, the gas sampling probe SP1 is selected by opening the gas sampling valve V1, an oil enriched fluid, the middle SP3 or/and top SP4 sampling probe is/are selected by opening respectively the middle sampling valve V3 or/and the top sampling valve V4, a water enriched fluid, the bottom sampling probe SP2 is selected by opening the bottom sampling valve V2.

However, depending on the flow regime prevailing in the main pipe and configuration of the pipe, each of the flow facing probes SP2, SP3 and SP4 can be selected for sampling predominantly a given heavy phase (water enriched fluid or oil enriched fluid).

The gas sampling probe SP1 placed at the top of the pipe and according to the flow direction is used for predominantly sampling a gas enriched fluid. This is due to the densities and therefore the inertial forces difference between liquid and gas, the gas sampling probe SP1 samples more gas, as the liquid will not change its flowing direction easily.

During this first step, the top port valve V5 is also preferably opened for letting flow the sampled fluid into the chamber 3 via the top port 3A. Alternatively, the bottom port valve V6 may be opened for letting flow the sampled fluid into the chamber 3 via the bottom port 3A. Alternatively, both port valves may be opened for letting flow the sampled fluid in the chamber 3.

Concomitantly, the piston 7A is actuated backward for sucking the sampled fluid in the chamber. Preferably, the piston is actuated at a speed that ensures a low differential pressure between the main pipe and the chamber.

Consequently, during the first step, the sampled fluid is transferred from the main pipe to the sampled chamber with a minimum pressure drop.

During the first step, the phase detector is used to control the type of the fluid phase flowing into the sample chamber.

According to a second step, the sampled fluid present in the chamber is enriched in the selected phase. This is performed by sucking the sampled fluid in the sample chamber and flushing back the unwanted phase back to the main pipe.

The sampled fluid sucked in the sample chamber settle down in layer due to the gravity. Preferably, the sampling apparatus is operated vertically for enhancing the gravity segregation of the various phases. In particular, the heavy phase (e.g. the water enriched fluid WE) flows down to the bottom port 3B via the annulus 9 between the piston 7A and the chamber 3 wall, while the lighter phase (e.g. the gas enriched phase GE and/or the oil enriched phase OE) stays near the top of the chamber.

The unwanted phases are flushed back to the main pipe either via the top port 3A or bottom port 3B depending on their relative density to the selected phase. The flushing operation is performed by moving the piston 7A upward in the chamber 3 and opening the corresponding port valve V5 or V6. The unwanted phase is flushed to the main pipe FL by one of the sampling ports SP1, SP2, SP3 or SP4 via its respective valve V1, V2, V3 or V4.

These steps may be repeated in an iterative process in order to accumulate a significant or sufficient volume of the fluid sample enriched in a selected phase in the sample chamber. Once again, the phase detector may be used for sensing the type of fluid leaving the sample chamber and deciding whether the sample chamber is predominantly filled with the selected phase to be sampled.

Generally, sampling a given phase enriched fluid in a multiphase fluid mixture flow is not possible as such due to the wide range of flow regimes and phase ratios that can be encountered. However, there is always a position in the flow line where a phase is predominantly present. Thus a good choice of the sampling probe may reduce the number of iterations for enriching the sampled fluid with a given phase.

According to a third step, a known volume of the fluid sample enriched in a selected phase is expelled by an outlet to an external application (e.g. shipping bottle, analyzing apparatus). This is performed by opening the outlet valve V7 and one of or both top V5 and bottom V6 port valve and moving the piston 7A upward in the chamber 3. The phase detector may be used for sensing the type of fluid leaving the sample chamber and confirming that it corresponds to the selected phase to be sampled.

During these steps, the sample is maintained at the main pipe pressure and temperature. This enables to avoid mass transfers between the different phases governed by thermodynamic laws.

Preferably, the pressure is maintained at the main pipe pressure value by leaving a connection opened via a sampling probe during all the process while more than one phase is present in the chamber (during sampling or flushing process). The pressure is controlled during the transfer of a selected phase sampled fluid to the application by manually or automatically adjusting the piston 7A speed and the outlet valve V7 opening.

In the hereinbefore described embodiment, the sampling apparatus comprises four sampling probes to sample the different phases. However, as it may be apparent to a man skilled in the art from the operation principle described hereinbefore, the sampling pipe may comprise less or more sampling probes, but at least one sampling probe. In particular and as an alternative (not shown), the sampling pipe may comprise one sampling probe having an adjustable height position within the sampling pipe. This single sampling probe coupled to the phase detector enables to position the sampling probe at an appropriate position within the pipe in order to predominantly select a fluid enriched in a given phase.

The single probe may be actively positioned in the desired phase through an hydraulically or mechanically controlled actuator depending on the response of the phase detector.

Though, the sampling apparatus was described in relation with a particular example consisting in sampling a significant sample volume of water, oil or gas flowing in a main pipe after a wellhead on the surface, it can obviously be used in other application, for example in sub-sea application, or in pipeline, or in conjunction with multiphase flow meter, etc . . . .

A particular application of the invention relating to the oilfield industry has been described. However, the invention is also applicable to others types of industry where there is a need to analyze a particular phase of a multiphase fluid mixture flowing into a main pipe (e.g. food industry, chemical industry . . . ).

The drawings and their description hereinbefore illustrate rather than limit the invention.

Any reference sign in a claim should not be construed as limiting the claim. The word "comprising" does not exclude the presence of other elements than those listed in a claim. The word "a" or "an" preceding an element does not exclude the presence of a plurality of such element.

The invention claimed is:

1. A sampling apparatus for sampling a fluid enriched in a selected phase from a multiphase fluid mixture flowing into a main pipe, the multiphase fluid mixture containing at least the selected phase and one other phase, the apparatus comprising:

a sampling arrangement for taking a fluid sample of the multiphase fluid mixture flowing into the main pipe, the sampling arrangement comprising at least one sampling probe positioned in an area of the sampling arrangement where the selected phase is predominantly present;

a sample chamber having a variable volume for collecting the fluid sample and letting the fluid sample settle by gravity into the fluid enriched in the selected phase and at least one other phase enriched fluid, and a valve manifold coupling the sampling arrangement to the sample chamber for driving the fluid sample in the sample chamber and for driving the fluid enriched in the selected phase to a sample outlet and the at least one other phase enriched fluid back to the main pipe.

2. A sampling apparatus according to claim 1, wherein the sampling apparatus further comprises a temperature controlling arrangement for maintaining the sample chamber and the valve manifold at the multiphase fluid mixture temperature of the main pipe.

3. A sampling apparatus according to claim 2, wherein the temperature controlling arrangement comprises a thermal insulator, a heating device and a temperature regulator.

4. A sampling apparatus according to claim 1, wherein:
the sampling arrangement comprises a sampling pipe adapted to be coupled to the main pipe, the sampling pipe comprising the at least one sampling probe,
the sample chamber having a variable volume and comprising a top port and a bottom port, and
the valve manifold coupling the sampling probe to the chamber and having a sample outlet for providing the fluid enriched in the selected phase, the valve manifold further comprising:
at least one probe valve coupling the sampling probe to a phase detector,
a top port valve coupling the phase detector to the top port,
a bottom port valve coupling the phase detector to the bottom port, and
an outlet valve coupling the phase detector to the sample outlet.

5. A sampling apparatus according to claim 4, wherein the piston is separated from the sample chamber wall by an annulus for letting a fluid present in the chamber flow down towards the bottom port.

6. A sampling apparatus according to claim 4 wherein the sampling pipe further comprises:
a bottom sampling probe positioned in an inferior part of the sampling pipe,
a middle sampling probe positioned in a center part of the sampling pipe,
a top sampling probe positioned in a superior part of the sampling pipe, and
the top, middle and bottom sampling probes facing the flow of the multiphase fluid mixture.

7. A sampling apparatus according to claim 6, wherein the sampling pipe further comprises a gas sampling probe positioned in the middle part of the sampling pipe and in an opposite direction relatively to the bottom, middle and top sampling probes.

8. A sampling apparatus according to claim 6, wherein the sampling pipe further comprises a gas sampling probe positioned in the superior part of the sampling pipe and in an opposite direction relative to the bottom, middle and top sampling probes.

9. A sampling apparatus according to claim 4, wherein at least one of the at least one sampling probes is adjustable within the sampling pipe.

10. A sampling apparatus according to claim 4, wherein the phase detector is an optical phase detector.

11. A sampling apparatus according to claim 4, wherein the sampling apparatus further comprises a sensor for measuring the volume of the sample chamber.

12. A sampling apparatus according to claim 11, wherein the sensor comprises means for measuring the position of the piston within the sample chamber.

13. A sampling apparatus according to claim 1, wherein the sample chamber comprises a piston and the sampling apparatus further comprises a piston actuator for displacing the piston within the sample chamber, the variable volume being defined by the position of the piston within the sample chamber.

14. A sampling method for sampling a fluid enriched in a selected phase from a multiphase fluid mixture flowing into a main pipe, the main pipe being fitted with a sampling apparatus comprising a sampling arrangement, a sample chamber, and a valve manifold, the sampling method comprising:
a first step comprising taking a fluid sample of the multiphase fluid mixture by coupling one sampling probe to the sample chamber and increasing the volume of the sample chamber, and letting the fluid sample settle by gravity in the sample chamber into the fluid enriched in the selected phase and at least one unwanted phase enriched fluid,
a second step comprising flushing at least one unwanted phase enriched fluid back to the main pipe by coupling the sample chamber to one sampling probe and decreasing the volume of the sample chamber,
repeating the first and second step to obtain a given quantity of the fluid enriched in the selected phase in the sample chamber, and
a third step comprising expelling the fluid enriched in the selected phase out of the sample chamber by coupling the sample chamber to the outlet and decreasing the volume of the sample chamber.

15. A sampling method according to claim 14, further comprising maintaining the sampling apparatus at the temperature of the multiphase fluid mixture flowing into a main pipe.

16. A sampling method according to claim 14, further comprising monitoring the phases of the fluid sample flowing in and out of the sample chamber.

17. A sampling method according to claim 14, wherein the sampling arrangement comprises a sampling pipe adapted to be coupled to the main pipe, the sampling pipe comprising:
a bottom sampling probe positioned in an inferior part of the sampling pipe,
a middle sampling probe positioned in a center part of the sampling pipe,
a top sampling probe positioned in a superior part of the sampling pipe, and
the top, middle and bottom sampling probes facing the flow of the multiphase fluid mixture; and
wherein the sampling method further comprises:
taking a water enriched fluid sample using the bottom sampling probe, or
taking an oil enriched fluid sample using the top or middle sampling probe.

18. A sampling method according to claim 17, wherein the sampling pipe further comprises a gas sampling probe positioned in the middle or superior part of the sampling pipe and in an opposite direction relative to the bottom, middle and top sampling probes; and
wherein the sampling method further comprises:
taking a gas enriched fluid sample using the gas sampling probe.

* * * * *